(12) United States Patent
Livneh

(10) Patent No.: US 8,012,154 B2
(45) Date of Patent: Sep. 6, 2011

(54) MODULAR ELECTROSURGICAL ADAPTORS AND MULTI FUNCTION ACTIVE SHAFTS FOR USE IN ELECTROSURGICAL INSTRUMENTS

(75) Inventor: Steve Livneh, Amherstburg (CA)

(73) Assignee: Bovie Medical Corporation, St. Petersburg, FL (US)

( * ) Notice: Subject to any disclaimer, the term of this patent is extended or adjusted under 35 U.S.C. 154(b) by 790 days.

(21) Appl. No.: 12/028,419

(22) Filed: Feb. 8, 2008

(65) Prior Publication Data

US 2008/0208246 A1 Aug. 28, 2008

Related U.S. Application Data

(60) Provisional application No. 60/888,918, filed on Feb. 8, 2007, provisional application No. 60/893,514, filed on Mar. 7, 2007.

(51) Int. Cl.
*A61B 18/14* (2006.01)
*A61B 17/28* (2006.01)

(52) U.S. Cl. ............................................. 606/52; 606/51

(58) Field of Classification Search .................... 606/51, 606/52

See application file for complete search history.

(56) References Cited

U.S. PATENT DOCUMENTS

| | | | | |
|---|---|---|---|---|
| 4,520,648 A * | 6/1985 | Gregory | .................... | 29/243.527 |
| 5,174,300 A * | 12/1992 | Bales et al. | .................... | 600/564 |
| 5,499,992 A * | 3/1996 | Meade et al. | .................. | 606/170 |
| 5,637,110 A * | 6/1997 | Pennybacker et al. | .......... | 606/46 |
| 5,961,514 A * | 10/1999 | Long et al. | ....................... | 606/41 |
| 6,409,728 B1 * | 6/2002 | Ehr et al. | .......................... | 606/51 |
| 6,679,882 B1 | 1/2004 | Kornerup | | |
| 7,131,978 B2 * | 11/2006 | Sancoff et al. | ................. | 606/139 |
| 7,367,976 B2 * | 5/2008 | Lawes et al. | .................... | 606/51 |
| 7,632,270 B2 * | 12/2009 | Livneh | .............................. | 606/51 |
| 2005/0137590 A1 * | 6/2005 | Lawes et al. | ..................... | 606/45 |
| 2005/0165443 A1 | 7/2005 | Livneh | | |

FOREIGN PATENT DOCUMENTS

DE 9422450 U1 1/2003
WO WO9724072 A1 7/1997

OTHER PUBLICATIONS

International Search Report, International Application No. PCT/US2008/001740, May 19, 2008, 3 pages.

\* cited by examiner

*Primary Examiner* — Linda C Dvorak
*Assistant Examiner* — Thomas Giuliani
(74) *Attorney, Agent, or Firm* — Howard & Howard Attorneys PLLC

(57) ABSTRACT

Forceps include a body, a surgical device, and a pair of handles. The surgical device is removably disposed within the body. The handles are pivotally attached to the handle body for articulating jaws on the surgical device, or grasping the forceps. The forceps accept monopolar, bipolar, or both monopolar and bipolar surgical devices. Wires are disposed within the surgical device for performing various types of electro-surgery. Additional wires are provided within the surgical device for providing the user with the ability to monitor various aspects of the surgical procedure. Spring contacts touch rings surrounding the surgical device for maintaining electrical contact with the surgical device while allowing the surgical device to rotate within the body.

10 Claims, 18 Drawing Sheets

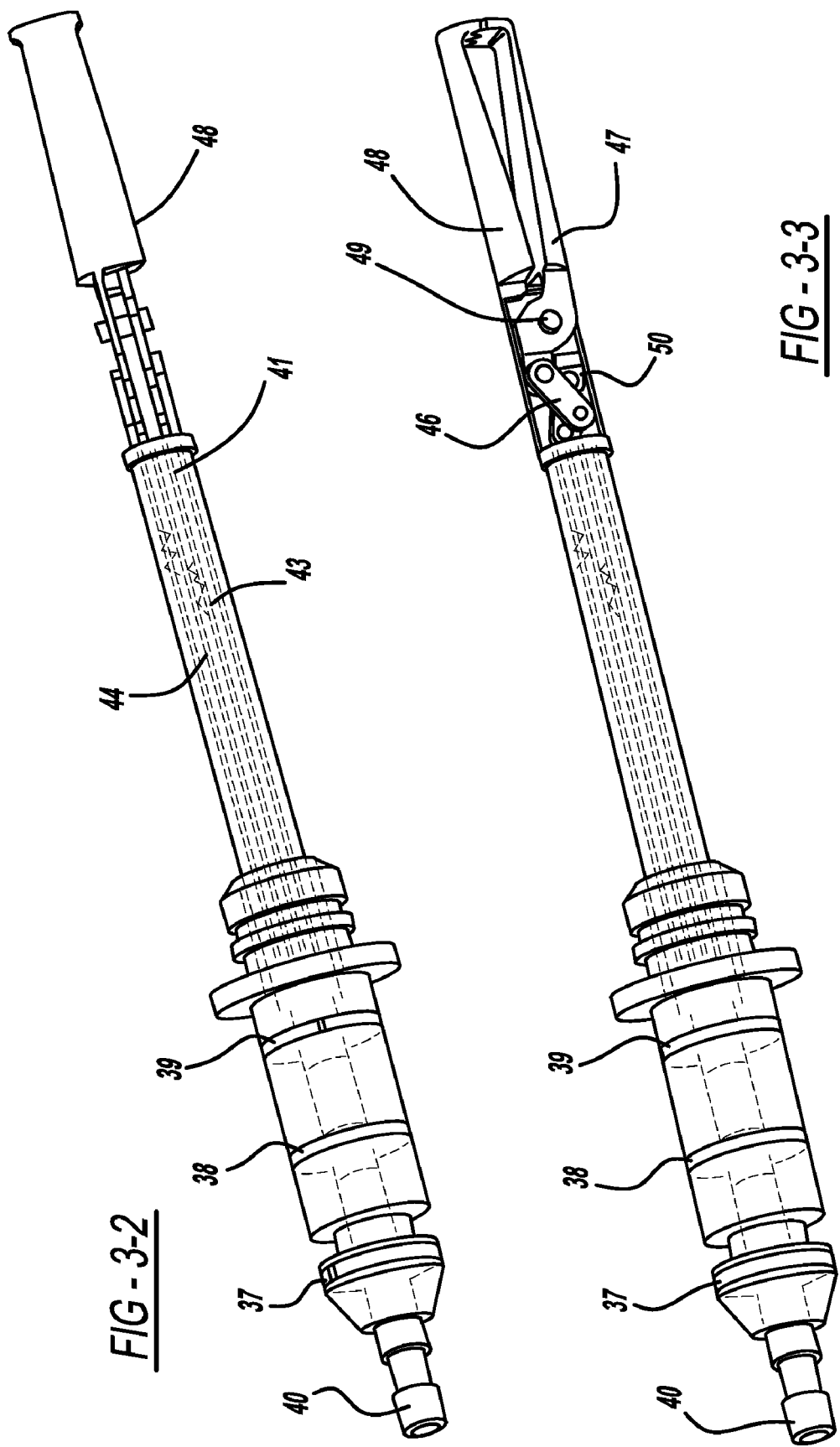

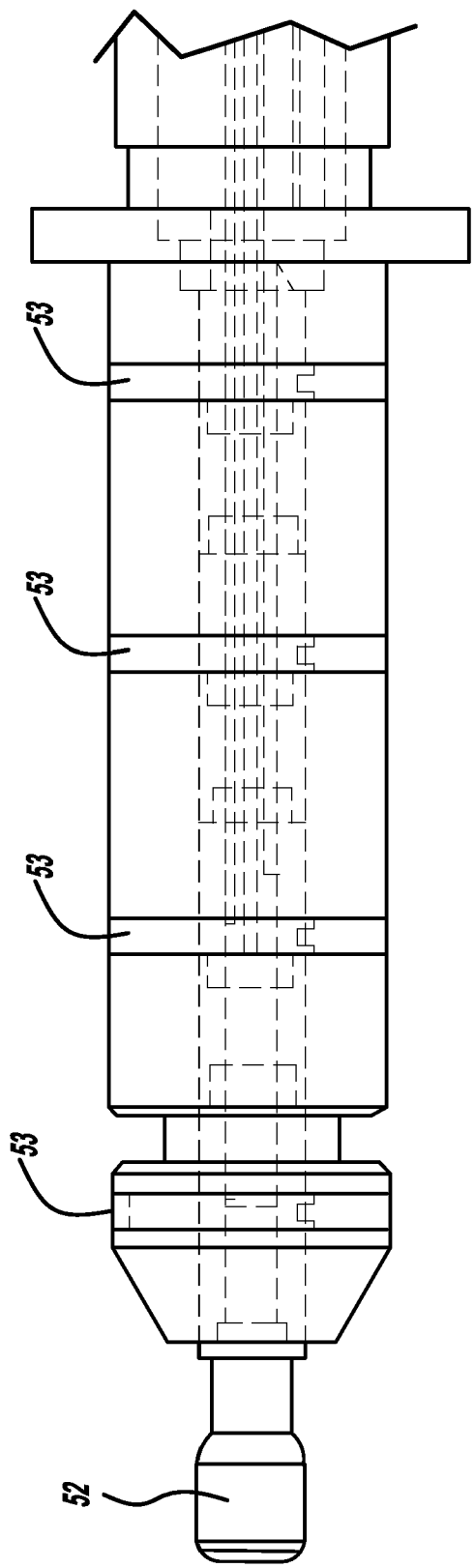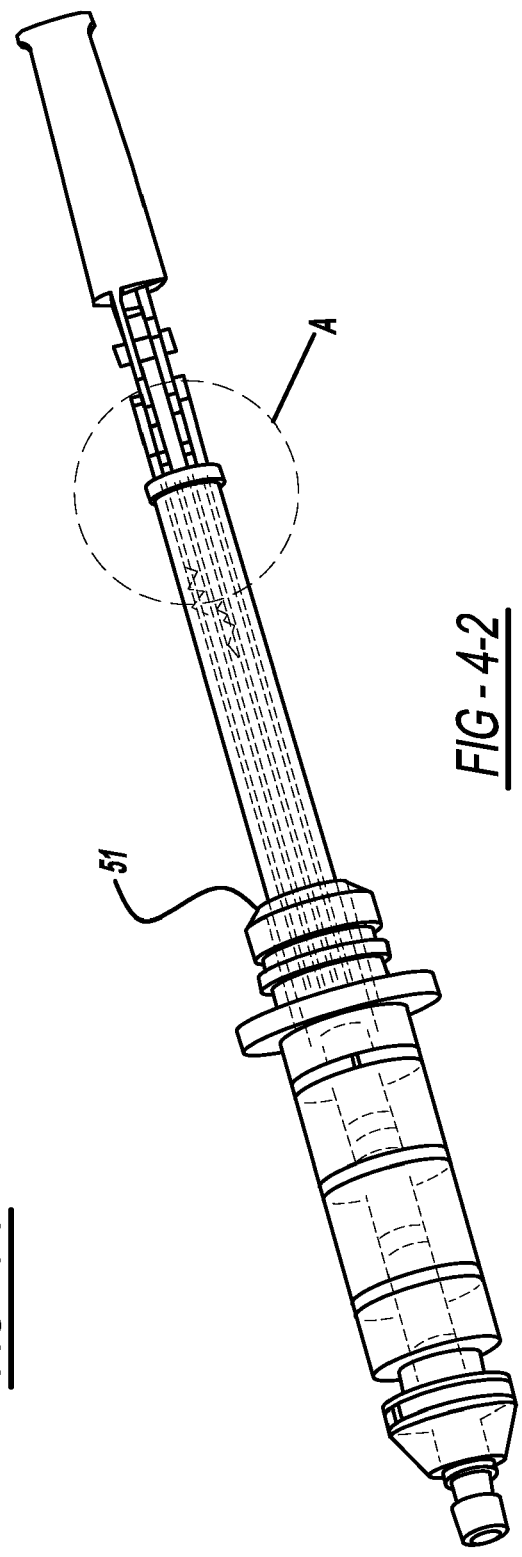
FIG-4-1
FIG-4-2

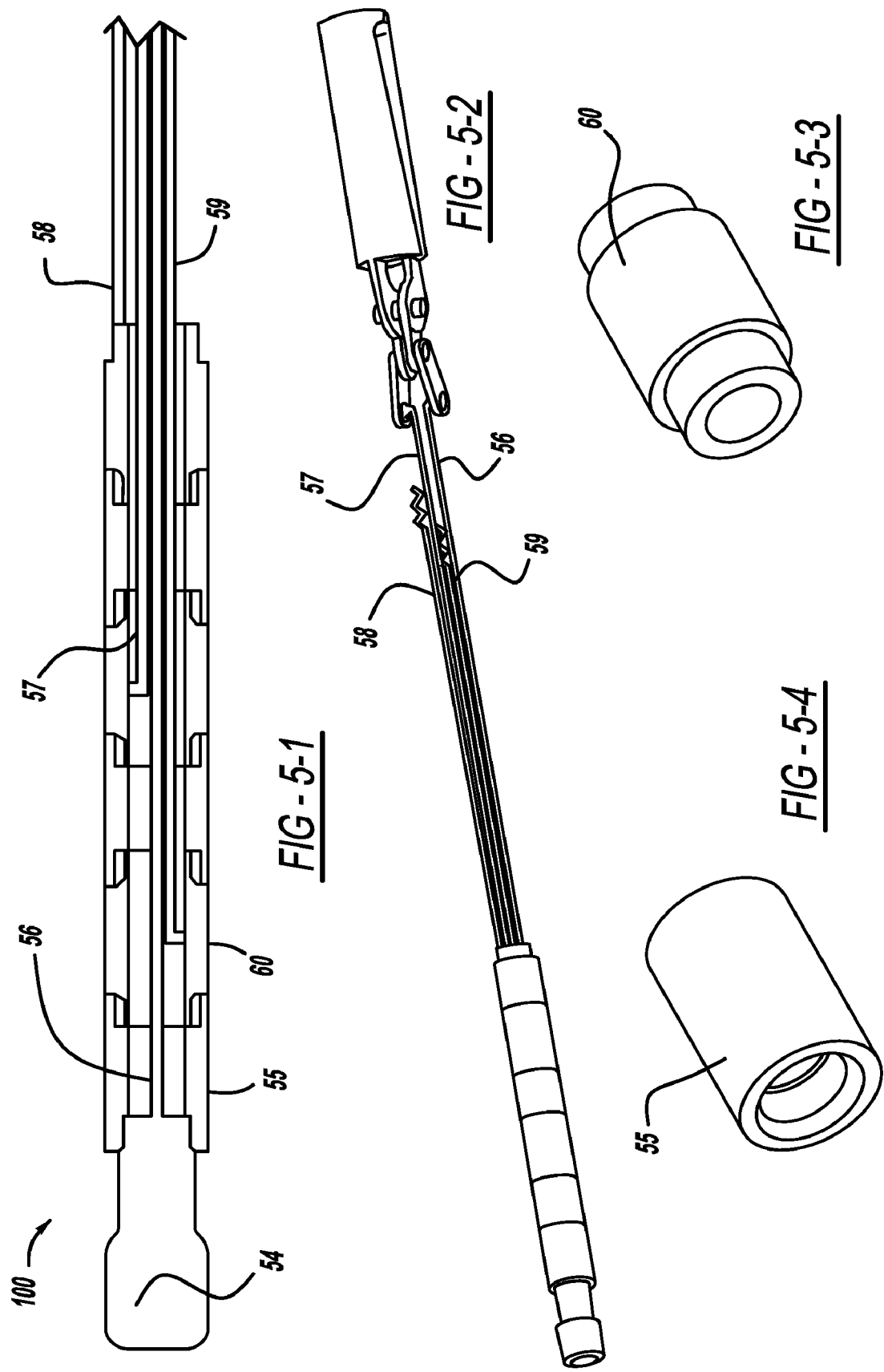

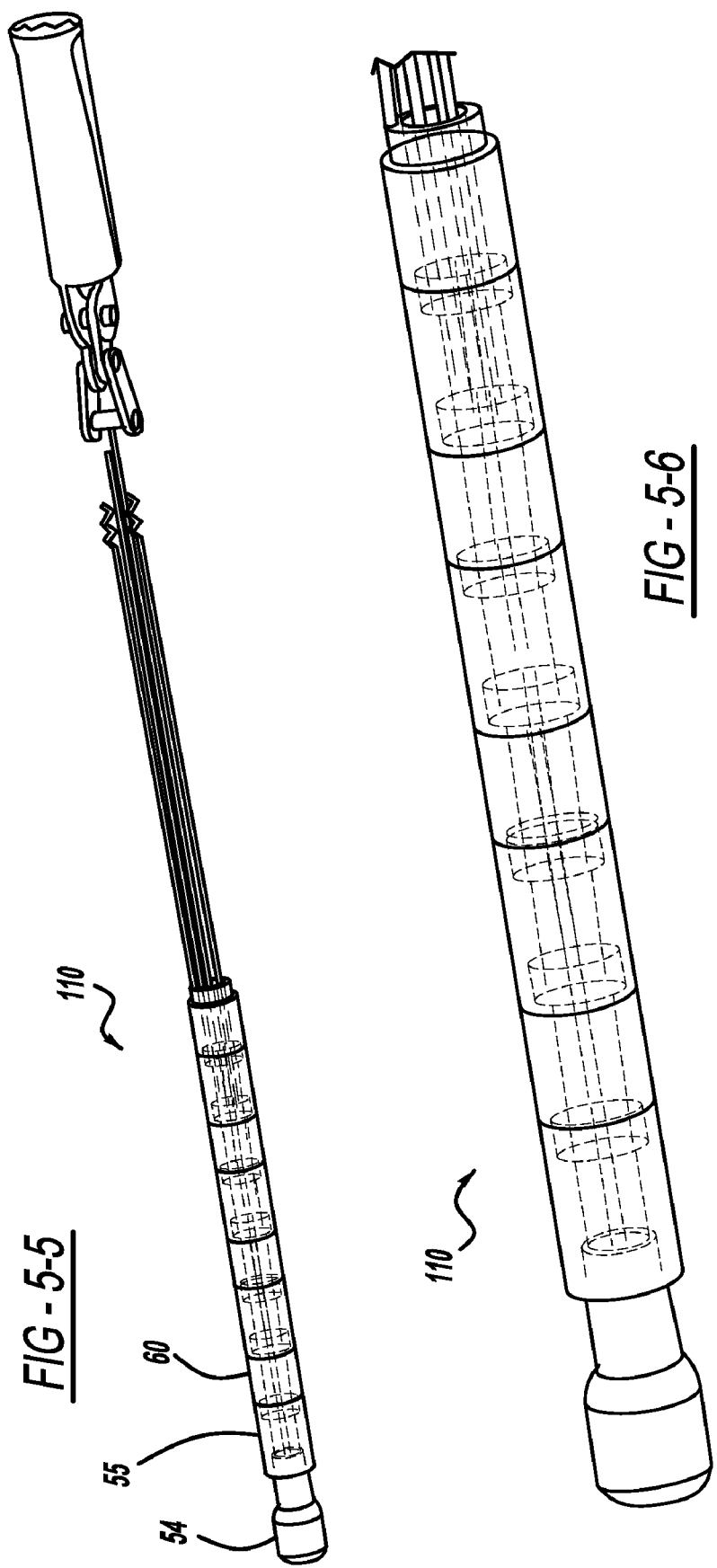

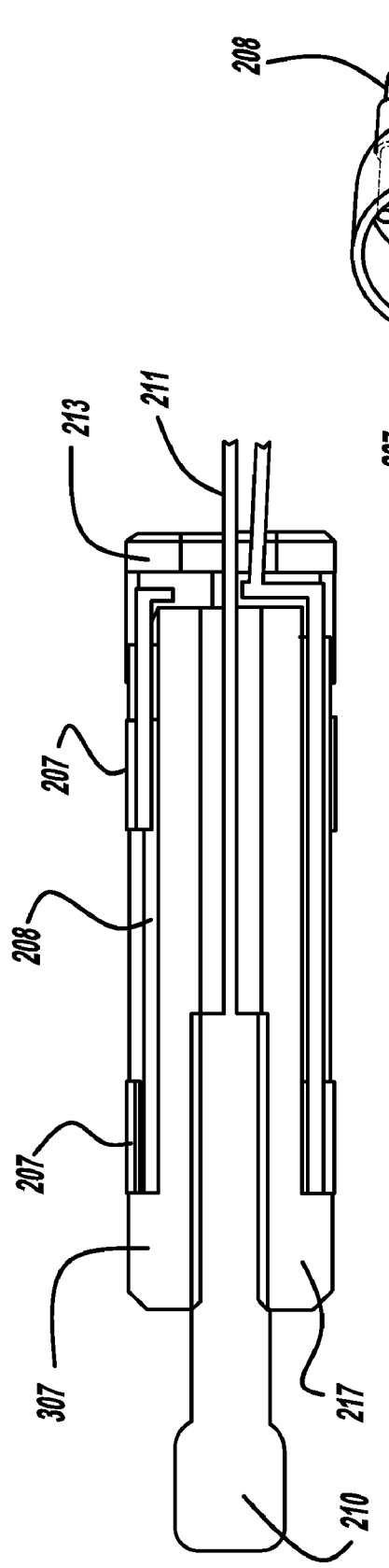
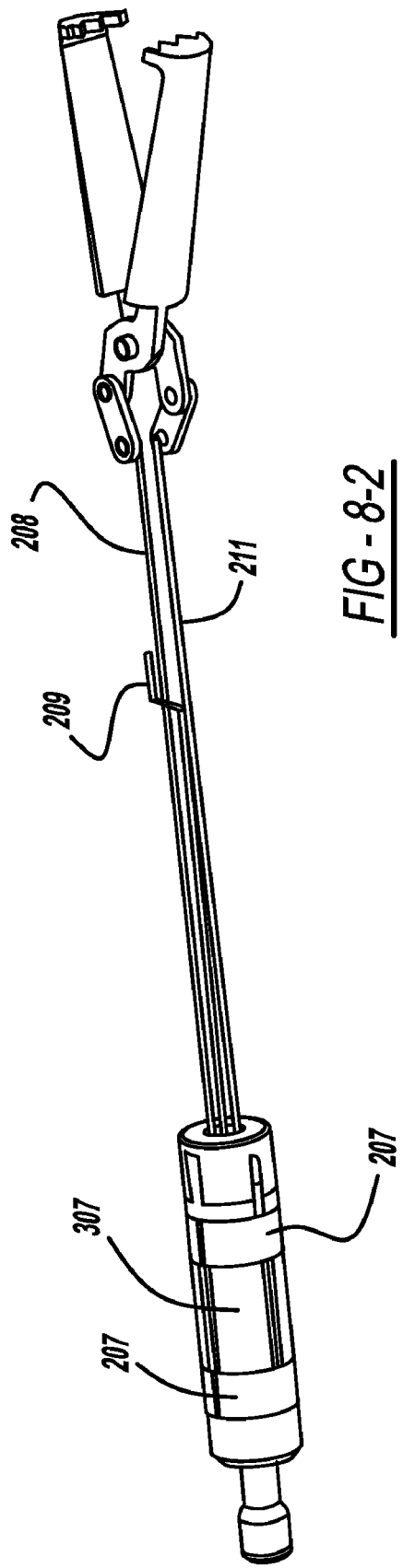
FIG-8-1
FIG-8-4
FIG-8-2

MODULAR ELECTROSURGICAL ADAPTORS AND MULTI FUNCTION ACTIVE SHAFTS FOR USE IN ELECTROSURGICAL INSTRUMENTS

CROSS-REFERENCE TO RELATED APPLICATION

The instant application claims priority to U.S. Provisional Patent Application Ser. No. 60/888,918, filed Feb. 8, 2007, and U.S. Provisional Patent Application Ser. No. 60/893,514, filed Mar. 7, 2007, the entire specifications of both of which are expressly incorporated herein by reference.

FIELD OF THE INVENTION

The present invention generally relates to electrosurgical instruments and more specifically to adaptors and shafts for use with electrosurgical instruments.

BACKGROUND OF THE INVENTION

Recent trends in electrosurgical instrumentation, both endoscopic and open surgery, require one or more conducting channels to control and monitor current and control desired functions which are related to active elements incorporated into advanced surgical instruments.

Due to increased costs, sterilization requirements, and environmental considerations, there is a growing demand for active surgical devices, i.e., devices that have jaws for grasping, cutting, and/or dissecting, clamps, electrodes, and/or the like that may be disassembled and are adaptable. These devices may have one or more elements which are removable for cleaning or sterilization, disposal, interchangeability, or alterations.

The electrical current types required for the elements of the surgical devices could be, but are not limited to monopolar and bipolar currents in all frequencies and wave forms and DC current. Conductive channels (e.g., wires) which have extra insulation may be useful to perform various measurements within the elements of the surgical devices, such as temperature measurement, current flow measurement, measurement of conductivity, measurement of resistance, impedance, pressure, liquid and gas flow, and/or the like. In other cases, power may be required for other types of elements, such as motors, heating elements, and/or the like.

Accordingly, there exists a need for new and improved systems and methods for providing or constructing electrosurgical devices which are adaptable and/or active that overcome at least one of the disadvantages of the prior art.

SUMMARY OF THE INVENTION

The present invention describes a system and a method to provide or construct surgical devices (e.g., electrosurgical devices) which are adaptable and/or active. The unique features of these devices are in the electrosurgical adaptors that allow attachment and detachment. In addition, sterilization of the elements and within compound shafts of the surgical devices may also be performed. Further, contacts and insulation arrangements within the adaptors, and related compound shafts, enable essential mechanical movements while being able to include a plurality of wire conductors. These wires convey currents and signals to and from the elements (e.g., jaws, tongs, electrodes, and/or the like). The specific designs of handles, adaptors, and compound shafts within the electrosurgical instruments permit unlimited rotation while allowing attachment/detachment of the elements from the electrosurgical instruments.

More specifically, the present invention also discloses the necessary details to construct attachable/detachable, multi function, active surgical devices. The devices may be attached or detached to a surgical handle which provides a plurality of electrical and mechanical connections. The mechanical and electrical connections may activate and connect the devices via electrosurgical adaptors, contacts, connectors, wires, cables or shafts that are within the detachable surgical devices. The surgical devices could perform a variety of mechanical movements (e.g., grasping, dissecting, and/or shearing), be rotated beyond 360 degrees, and perform electro-cautery, electro-dissecting, coagulation, or homeostasis functions on a variety of tissue types. Further, these attachable/detachable devices may be equipped with extra electrical contacts and wires, which convey extra power, control and measurement to and from the elements of the electrosurgical devices, through the handle, via a generator. However, any other desired and related input or control unit may also be provided for use with the detachable devices.

Further areas of applicability of the present invention will become apparent from the detailed description provided hereinafter. It should be understood that the detailed description and specific examples, while indicating the preferred embodiment of the invention, are intended for purposed of illustration only and are not intended to limit the scope of the invention.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1-2 shows an enlargement of detail area A of FIG. 1-1, showing a cross-section through the electrosurgical adaptor and adjacent handles;

FIG. 2-1 shows a side view of the modular electrosurgical forceps;

FIG. 2-2 shows an enlargement of detail area B of FIG. 2-3;

FIG. 2-3 shows a cross-sectional top view of the forceps taken along line A-A of FIG. 2-1;

FIG. 3-1 shows an enlarged cross-sectional view of the electrosurgical adaptor, configured for a bipolar application with two additional wires;

FIG. 3-2 shows a transparent view of a detachable electrosurgical device, configured for a bipolar application with two extra wires and contacts;

FIG. 3-3 shows another view of the bipolar detachable, electrosurgical device with two extra contacts and wires;

FIG. 4-1 shows a side view of the electrosurgical adaptor with components shown in transparency and configured for the monopolar application with four extra contacts and wires;

FIG. 4-2 shows a perspective view of the electrosurgical adapter with components shown in transparency, with four extra contacts and wires;

FIG. 4-3 shows another perspective view of FIG. 4-2 above;

FIG. 4-4 shows an enlargement of detail area A of FIG. 4-2;

FIG. 5-1 shows a typical section through a compound bipolar shaft with two extra wires;

FIG. 5-2 shows an assembly of a bipolar shaft and jaws, with two extra wires;

FIG. 5-3 shows a conducting shaft connector;

FIG. 5-4 shows a perspective view of a non-conducting shaft connector;

FIG. 5-5 shows a perspective view of an assembly of a monopolar shaft and jaws, with four extra wires;

FIG. 5-6 shows a partial perspective view of a compound monopolar shaft with four extra wires;

FIG. 6-1 shows an elevational view of an adaptor body;

FIG. 6-2 shows a sectional view taken along line A-A of FIG. 6-1;

FIG. 6-3 shows a perspective view of a spring contact;

FIG. 6-4 shows a perspective view of a contact ring;

FIG. 6-5 shows a perspective view of an adaptor body;

FIG. 6-6 shows an enlargement of detail area B of FIG. 6-2;

FIG. 6-7 shows an enlargement of detail area C of FIG. 6-1;

FIG. 7-1 shows a cross-sectional side view of an alternative embodiment of the modular electrosurgical forceps, including an electrosurgical adaptor and a pair of handles;

FIG. 7-2 shows enlargement of detail area A of FIG. 7-1, showing a cross-section through the electrosurgical adaptor and adjacent handles;

FIG. 8-1 shows a cross-sectional view of a three-contact compound shaft of the alternative embodiment of FIG. 7-1;

FIG. 8-2 shows an isometric view of the compound shaft, contacts, wires and bipolar jaws of the alternative embodiment of FIG. 7-1

FIG. 8-3 shows an exploded isometric view of the elements of FIG. 8-2 of the alternative embodiment of FIG. 7-1;

FIG. 8-4 shows a view of the contact ring and the wired connected to the contact ring;

FIG. 9-1b shows an end view of a non-conductive core for use with two rings;

FIG. 9-1c shows a perspective view of the non-conductive core for use with two rings;

FIG. 9-2 shows a perspective view of an alternative non-conductive core for use with four rings;

FIG. 9-3a shows a front perspective view of an adapter;

FIG. 9-3b shows a rear perspective view of an adapter;

FIG. 9-3c shows an end view of an adapter;

FIG. 9-3d shows a sectional view taken along line A-A of FIG. 9-3c; and

FIG. 9-4 shows a perspective view of a contact ring.

The same reference numerals refer to the same parts throughout the various Figures.

DETAILED DESCRIPTION OF THE INVENTION

Figure 1:
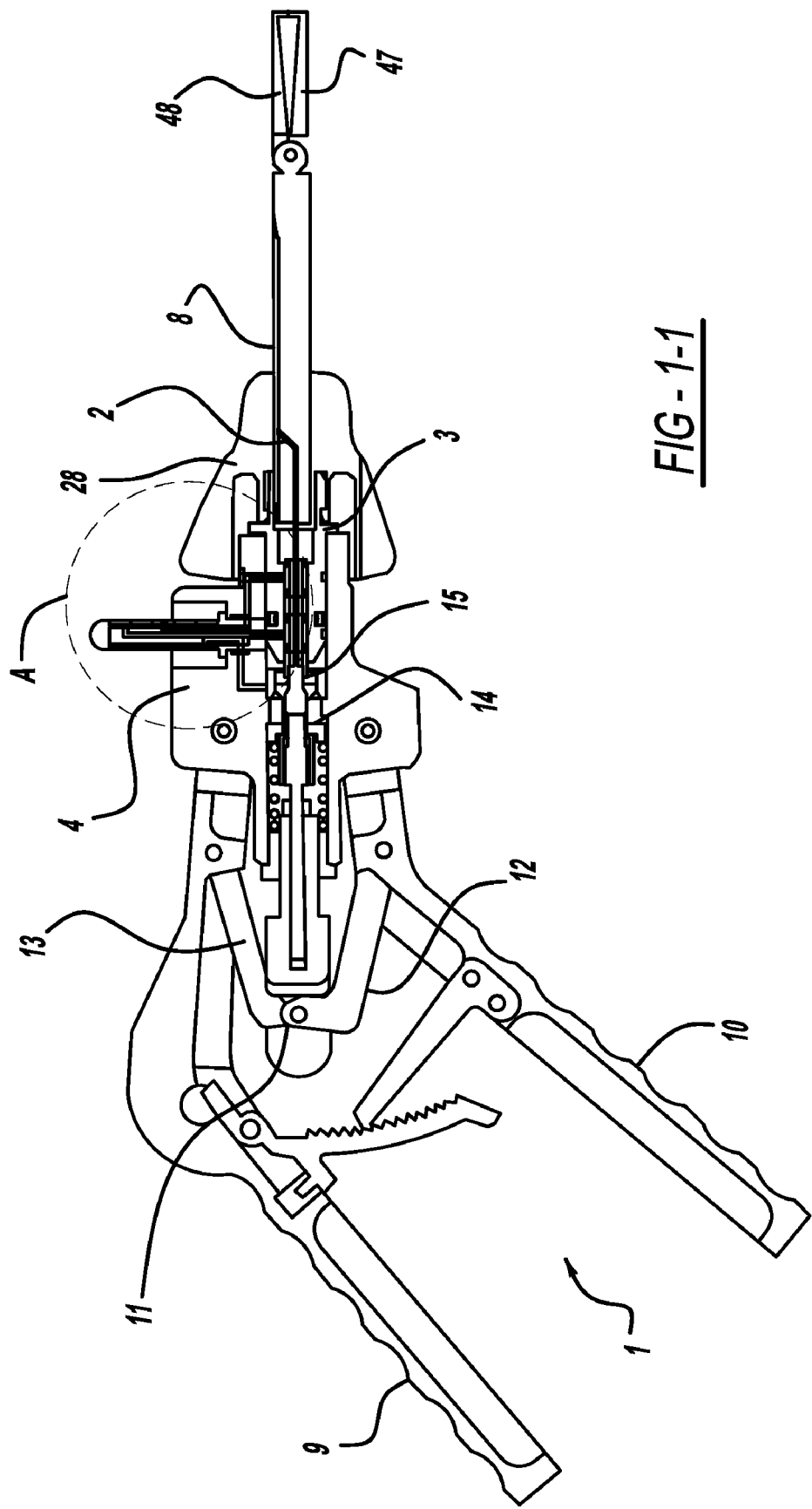
FIG. 1-1 shows a general cross-sectional side view of modular electrosurgical forceps, including an electrosurgical adaptor and a pair of handles.

The following description of the preferred embodiment(s) is merely exemplary in nature and is in no way intended to limit the invention, or uses. Referring to the Figures generally, wherein like numerals indicate like parts throughout the several views, and specifically to FIG. 1, an electrosurgical forceps is shown generally 1.

The forceps 1 include a handle body 4, a surgical device 2, and a pair of handles 9, 10. The surgical device 2 is removably disposed within the handle body 4. The handles 9, 10 are pivotally attached to the handle body for articulating jaws 47, 48 on the surgical device 2, or grasping the forceps 1.

Figures 1, 2:
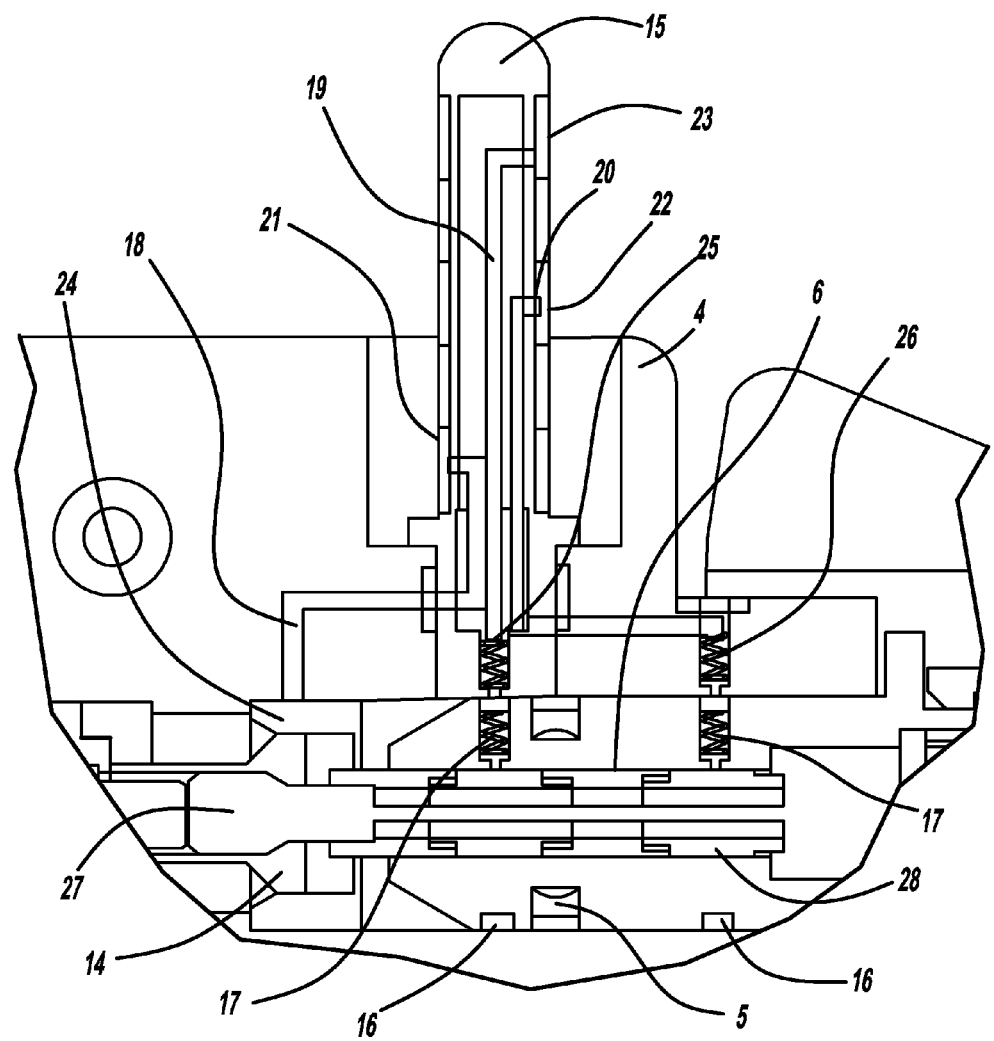

The surgical device 2 includes an adaptor body 3, preferably from non-conductive material such as polymer or ceramic, which is attached to the handle body 4 via a locking piece 5, as shown in FIG. 1-2. The adaptor body 3 defines a hollow passage 6. The hollow passage 6 allows reciprocal movements of compound shaft assembly 7 within a tubular element 8. Reciprocal movements are caused by closing or opening the handles 9 and 10 with respect to one another. When the handles 9 and 10 are closed, a stem assembly 11 is pulled proximally via links 12 and 13 and the retreat of a collet 14, which pulls an end 27 of compound shaft assembly 7 proximally.

FIG. 1-2 is a cross-section view, taken through the handle body 4 and the adaptor body 3, which shows a power plug assembly 15. The electrosurgical adaptor body 3 includes two contact rings 16 and spring contacts 17. Insulated wires 18, 19, 20, respectively, that are connected with axial rings 21, 23, 22 respectively, carry current from the power plug assembly 15 to a collet housing 24 and body spring contacts 25, 26.

Spring contacts 25, 26, and the collet housing 14, carry current to the contact rings 16 and the collet 14, respectively. Spring contacts 17, disposed within the adaptor body 3, carry currents to shaft conducting connectors and an end 27 of the compound shaft 7.

Torque is applied to the tubular element 8 or a rotation knob 28, shown in FIG. 2-1, which allows the surgical device 2 to rotate within handle body 4 while retaining continuous contacts from the power plug assembly 15 through the wires, housing, contacts and/or conductors. Therefore, independent currents may be conveyed via the incorporation of extra wires 33, 34 for other functions as stated above (e.g., see FIG. 2-3).

FIG. 2-2 shows a monopolar activating shaft 29, attached to an end 27 of the compound shaft assembly 7. The activating shaft 29 causes opening and closing of jaws 30, 31, via links 32, which act in concert with relative positions of the handles 9, 10 and a mechanical train, i.e., links 12, 13, stem assembly 11, collet 14, and/or the like.

Figures 1, 2:
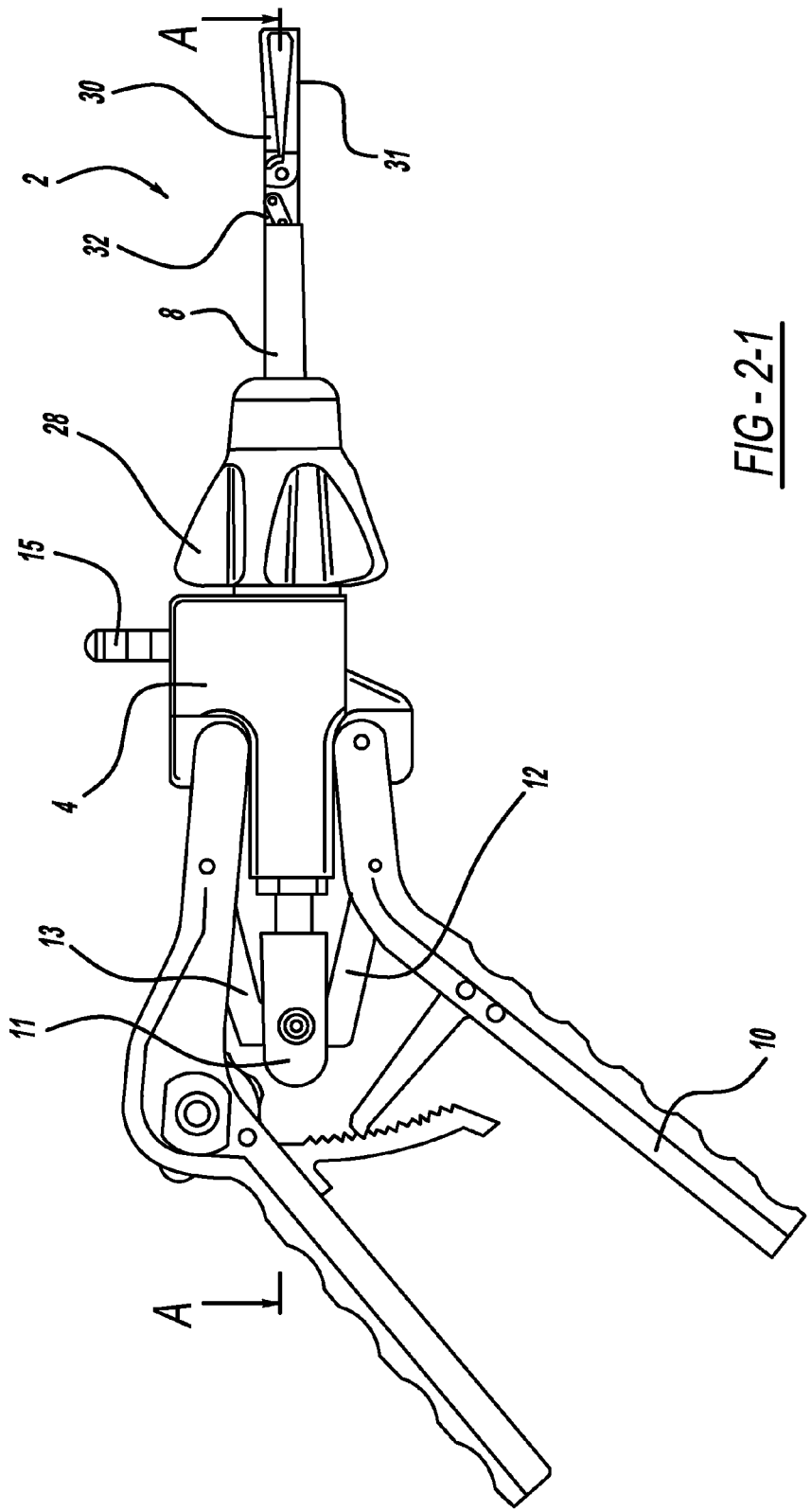
Figure 2:
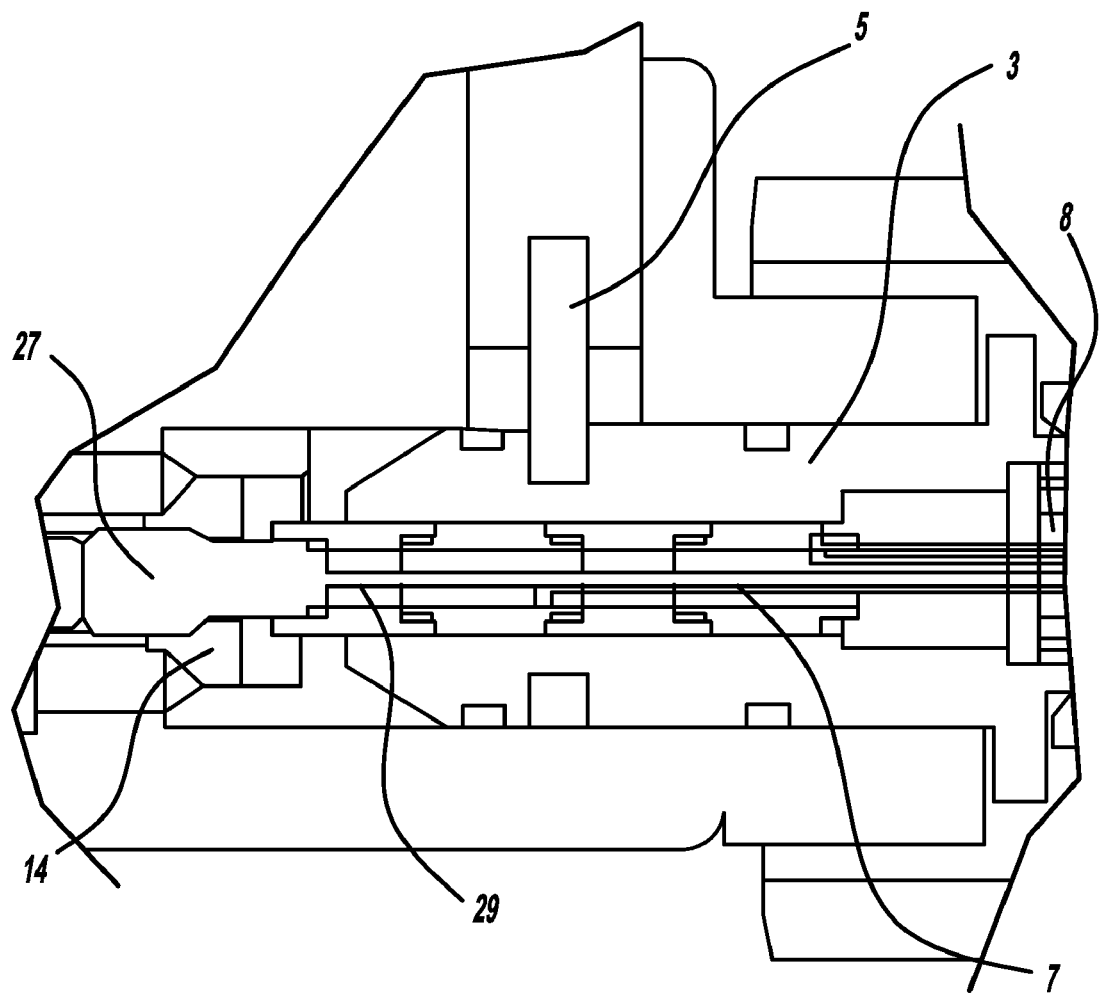
Figures 2, 3:
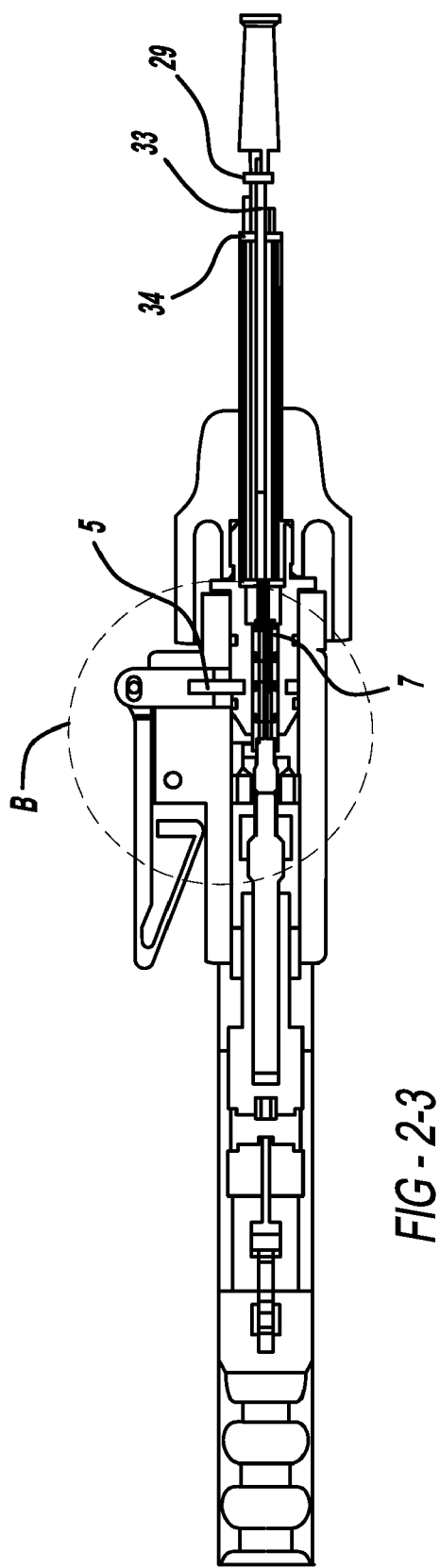
Figures 1, 3:
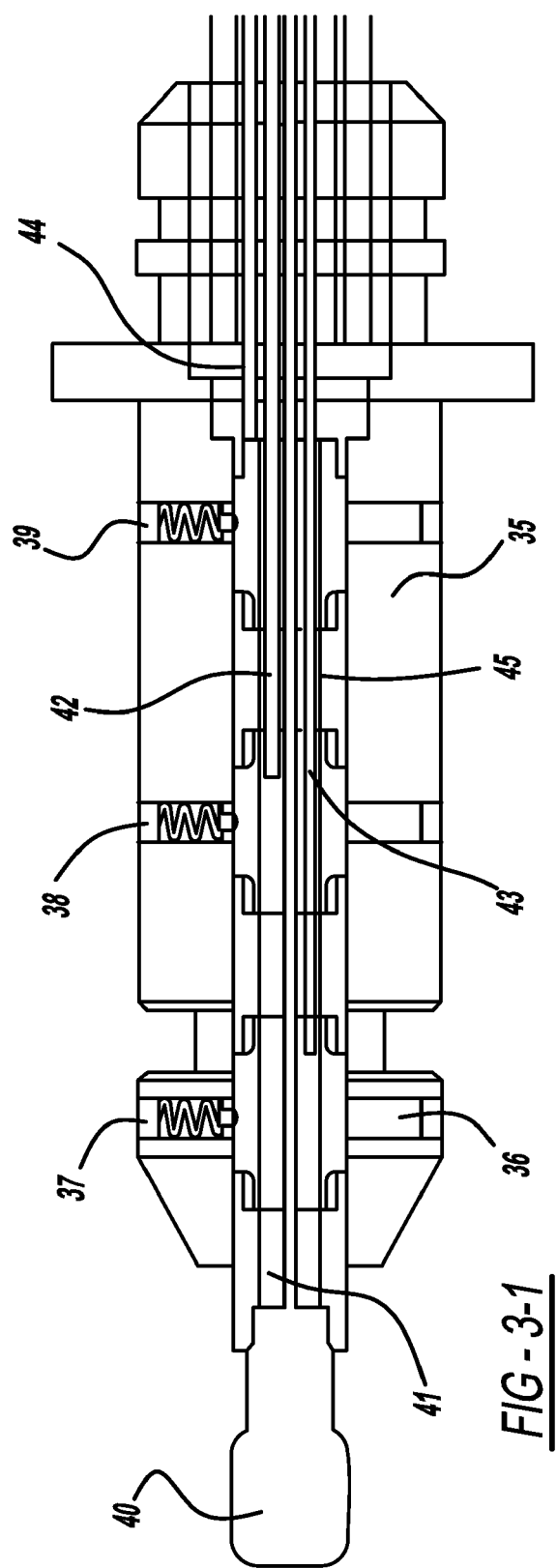

FIGS. 3-1, 3-2, and 3-3 show details of another example, in this case, a bipolar detachable device with two extra wire channels. Additionally, the handle body may be constructed to allow an insulated passage for a plurality of the conductive wires.

In this specific case, the adaptor body 35, carrying three contact rings 37, 38, 39, is housing a compound shaft 45 as shown. The shaft end 40 receives a positive current and is attached to conductive, insulated wire 41, driving link 46 and causing movement of jaw 47, rotated on insulated pin 49. Negative wire 42 similarly drives jaw 48 via link 50. Thus, while retaining insulation throughout, except when contacts are required for continuity, jaws 47, 48 will be charged in a bipolar fashion. Extra wires 43 and 44 allow other desired functions, as mentioned earlier, to be performed.

FIGS. 4-1, 4-2, 4-3, and 4-4 show another embodiment of a monopolar electrosurgical attachable device 51, where a compound shaft end 52 is connected to a positive electrical source via a handle body. Four contact rings 53 allow for the connection and/or application of other desired functions.

Figures 1, 6:
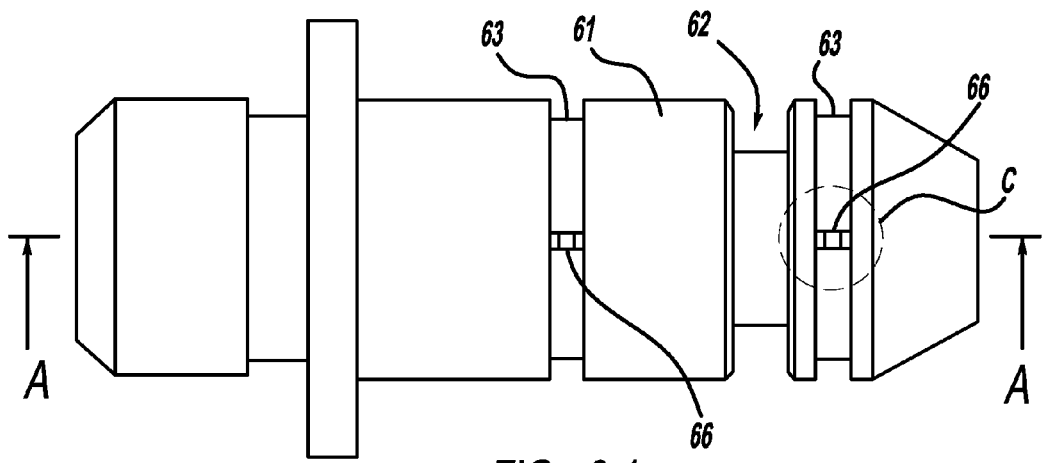
Figures 2, 6:
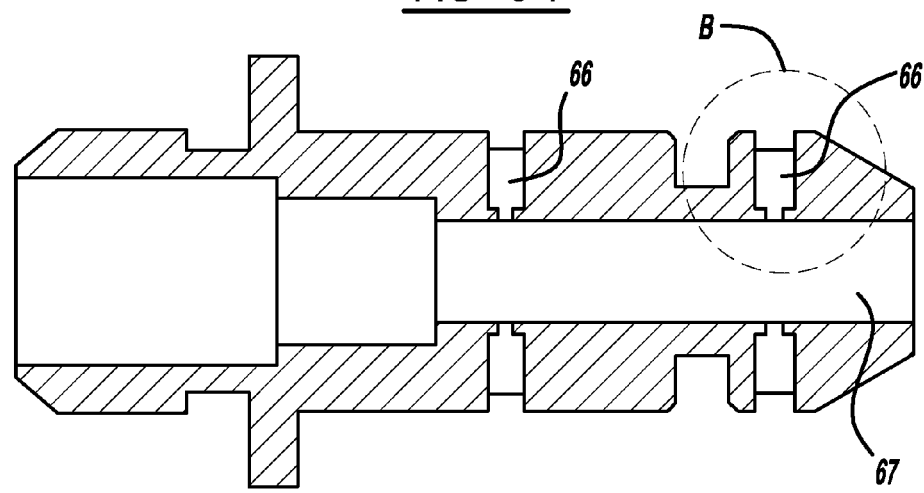
Figures 3, 6:
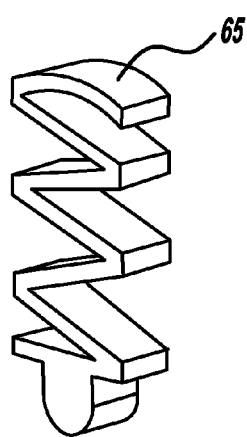
Figures 4, 6:
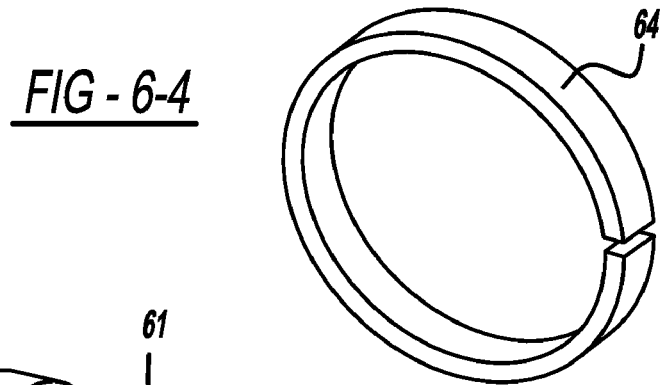
Figures 5, 6:
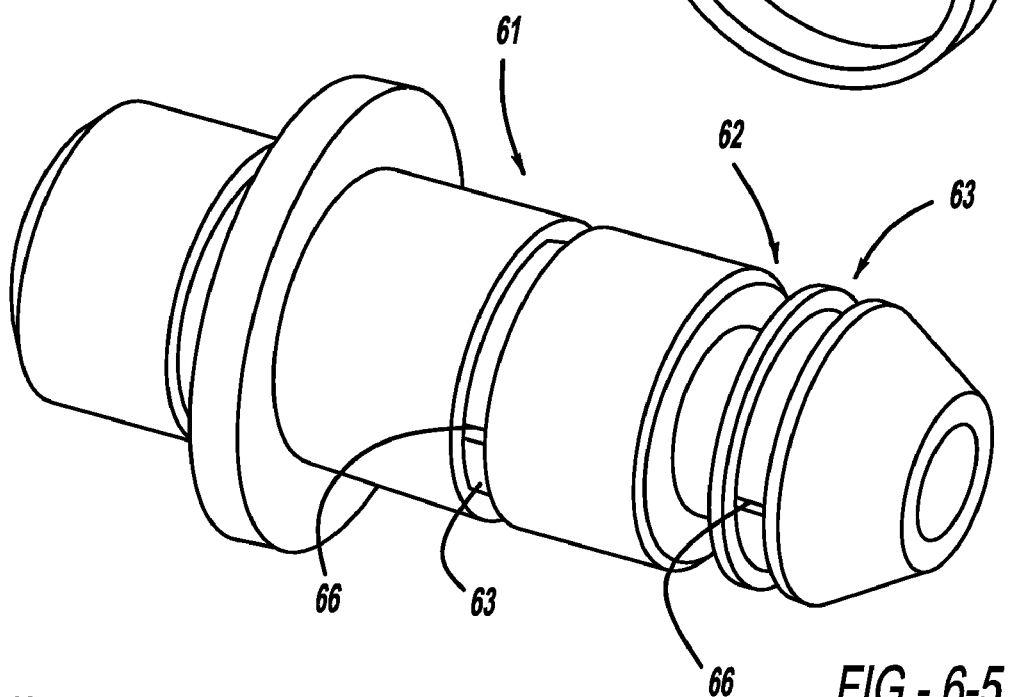
Figure 6:
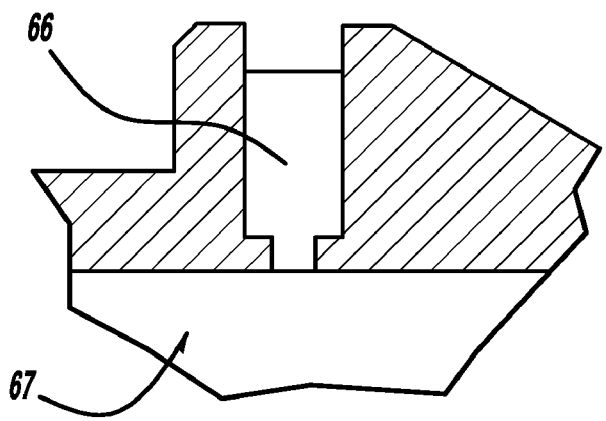

FIGS. 5-1 and 5-2 show a bipolar compound shaft 110 with two extra wires 58, 59. When an end 54 of the compound shaft 110 is securely attached to a non-conducting shaft connector 55, the whole shaft assembly and other wires, 57, 58, 59 are advanced within the adaptor body. The wires 56 and 57 activate and charge the jaws 47, 48, while the wires 58 and 59 are available for other tasks. Note that shaft end 54 and non-conductive and conductive connectors 55, 60, respectively, are attached rigidly.

FIGS. 5-5 and 5-6 show a construction of a monopolar compound shaft 110.

Figures 6, 7:
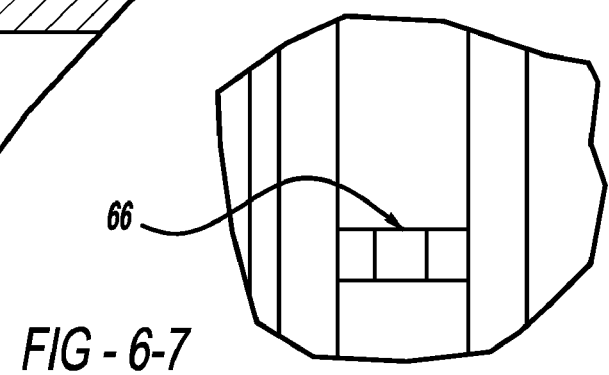
Figures 1, 7:
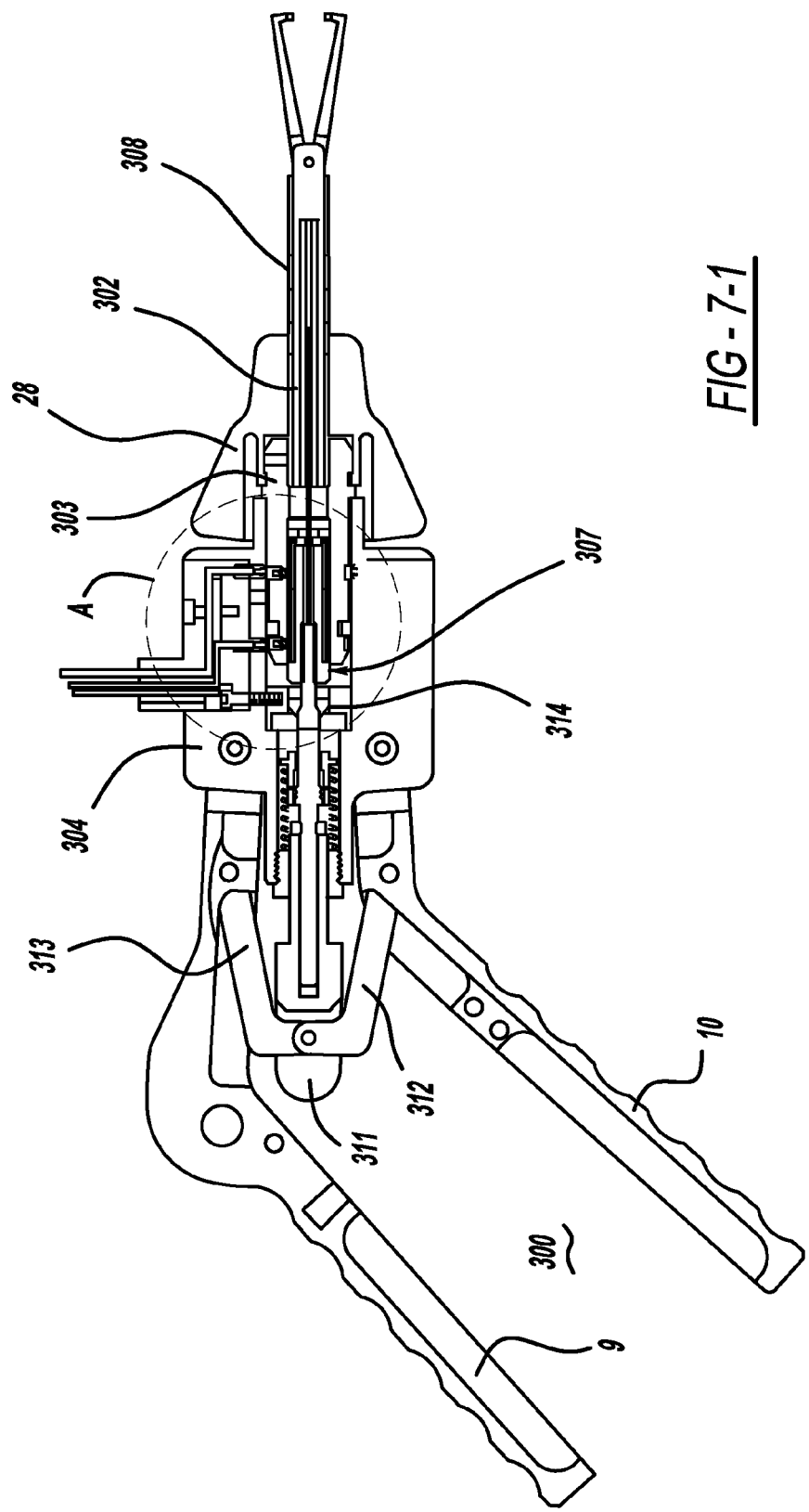
Figures 2, 7:
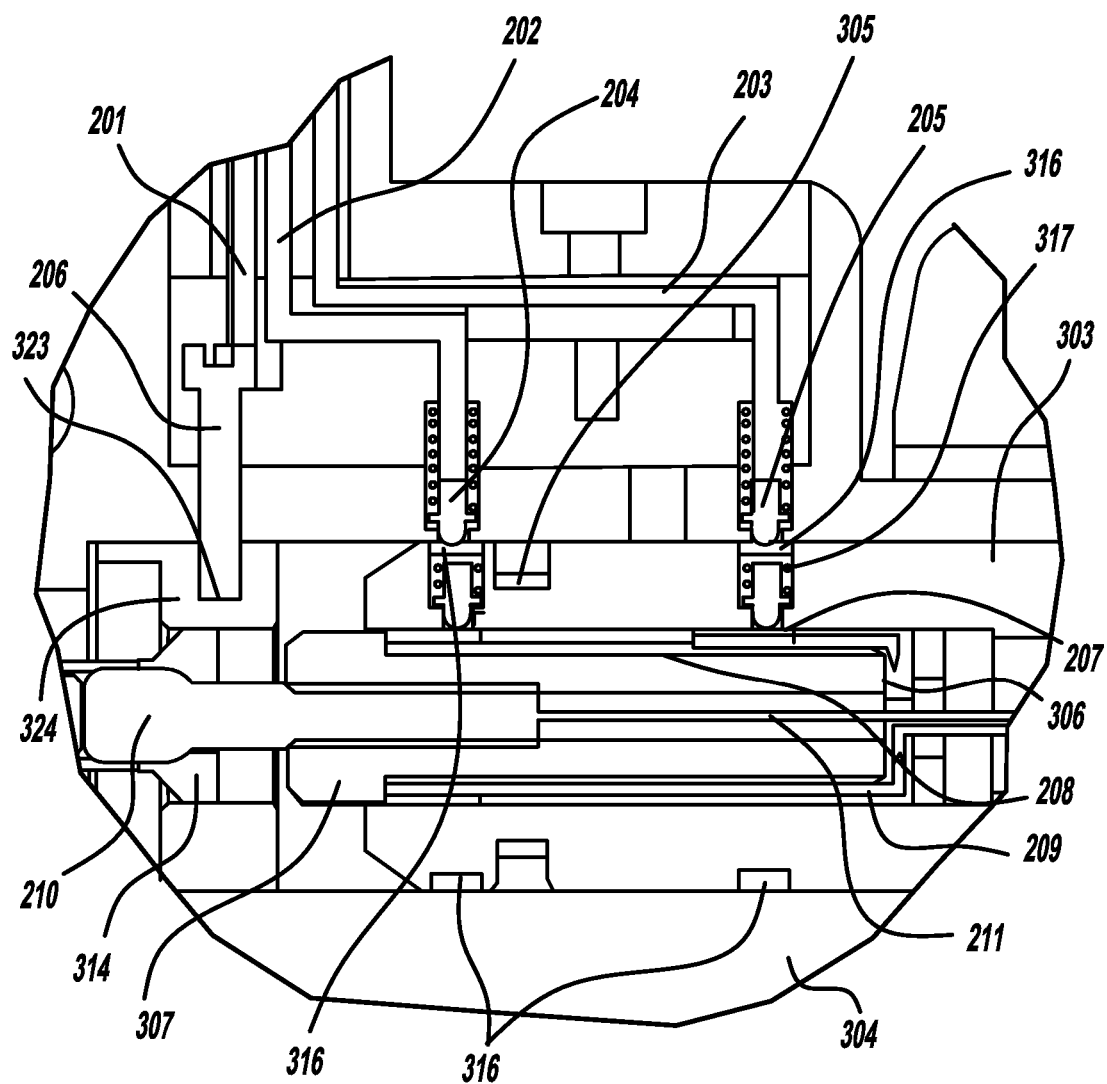

FIGS. 6-1 through 6-7 show a non-conductive adaptor body 61, defining a circumferential locking groove 62 and a contact ring groove 63. The adaptor body 61 defines a hole 66 within the contact ring groove 63. A spring contact 65, as illustrated in FIG. 6-3, is seated within the hole 66. A contact ring 64 (e.g., see FIG. 6-4) contacts and compresses the spring contact 65 within the hole 66 to conduct current to or from the compound shaft 100, 110, within a passage, defined in the adaptor body 61.

FIG. 7-1 shows a cross-sectional side view through an alternative embodiment of the modular electrosurgical forceps 300. The forceps 300 include a detachable endoscopic bipolar surgical device 302. The surgical device 302 of this embodiment is rotatable, while maintaining electrical contact. The surgical device 302 includes an adaptor body 303, preferably formed from non-conductive material such as polymer or ceramic, which is attached to a handle body 304 via a locking piece 305, as shown in FIG. 7-2. The adaptor body 303 defines a hollow passage 306. The hollow passage 306 allows reciprocal movements of a compound shaft assembly 307 within a tubular element 308. The reciprocal movements result from closing and/or opening the handles 9, 10. In this embodiment, closure of the handles 9, 10 causes the stem assembly 311 to be pulled proximally via links 312 and 313. As the links 312, 313 pull the stem assembly 311 proximally, the stem assembly 311 pulls a collet 314 proximally. The collet 314, which grasps the compound shaft 307, pulls the compound shaft 307 proximally.

FIG. 7-2 shows an enlarged cross-sectional view taken through the handle body 304 and the adaptor body 303. Insulated wiring 202, 203 connect to spring contacts 204, 205, respectively. The spring contacts 204, 205 touch contact rings 316, disposed on the compound shaft 307. Therefore, the adaptor body 303 of the forceps 300 includes two contact rings 316 and spring contacts 317. Insulated wire 201 connects to a collet contact 206. The collet contact 206 extends into a groove 323 defined by a collet housing 324. The collet housing 324 is disposed within the hollow passage 306. The collet housing 324 is formed from a metallic, or other conductive material. The contact rings 207 are connected to wires 208, 209. A cable end 210, which extends from the compound shaft 307, is conductive and conveys current to wire 211.

Figures 3, 4:
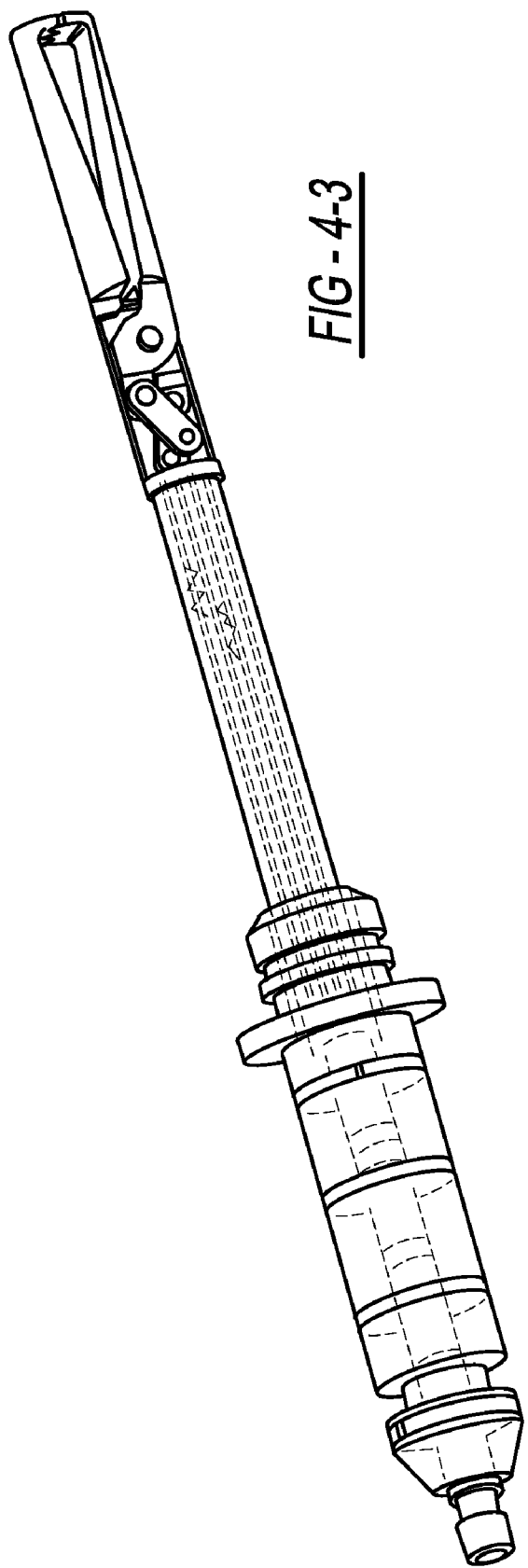
Figure 4:
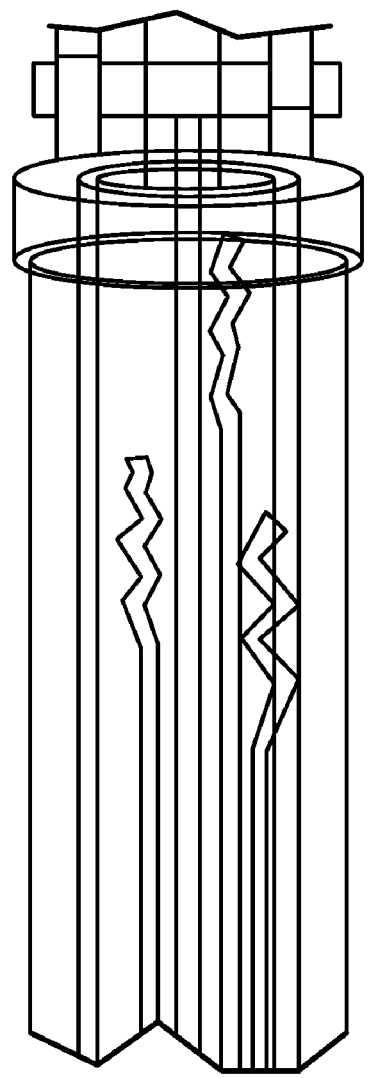
Figures 3, 8:
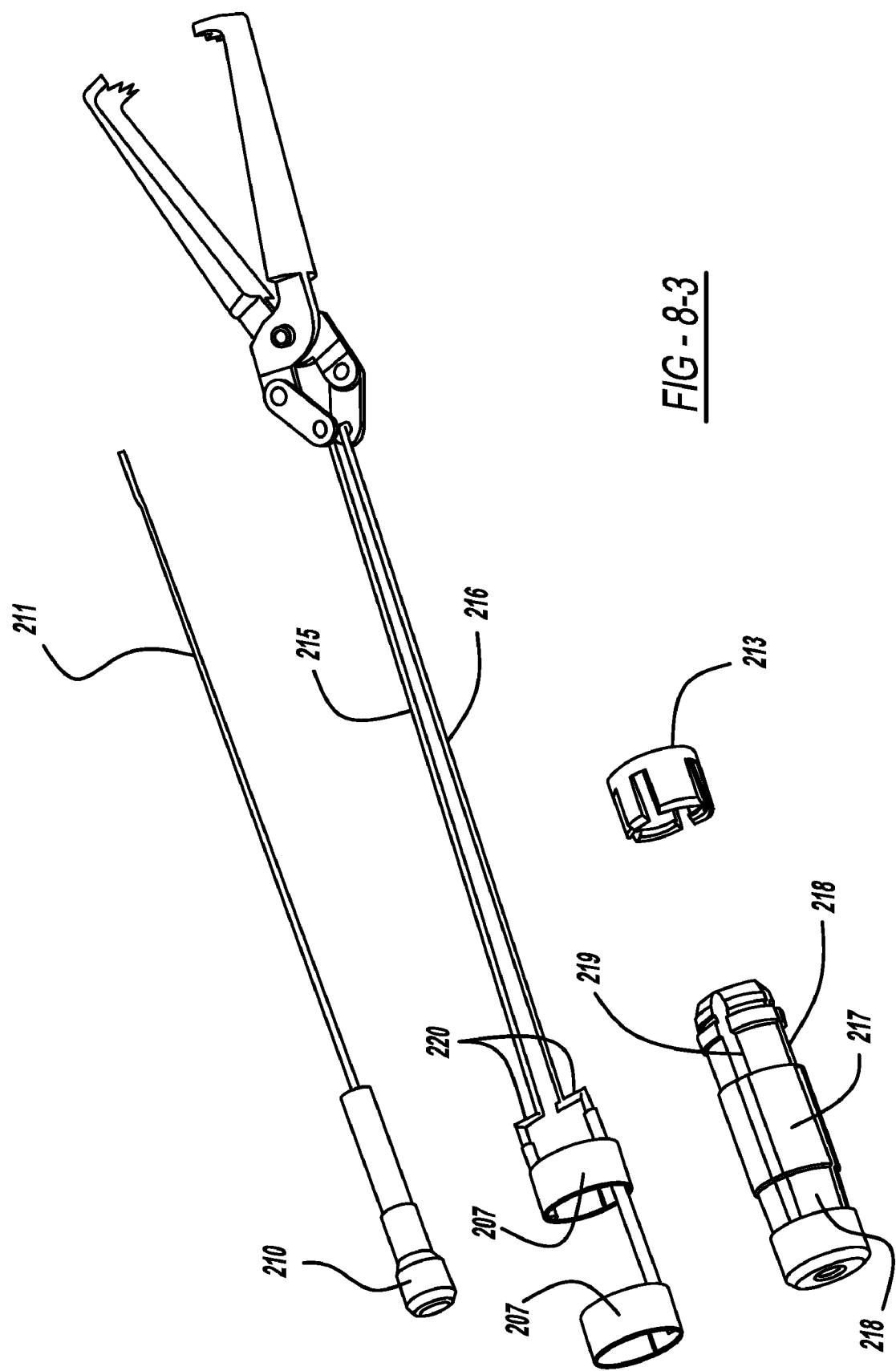

Referring to FIG. 8-4, a typical contact assembly 212 is shown. The assembly 212 includes a contact ring 207 which is connected to an insulated wire 208. The insulated wire 208 includes an end which is exposed and soldered, crimped, welded, or otherwise attached to the contact ring 207.

Referring to FIGS. 8-1 and 8-2, the compound shaft assembly 307 is shown. The compound shaft assembly 307 includes a cable end 210 which is connected to a non-conductive core 217. Two contact rings 207 are placed in recesses 218 which are defined in the non-conductive core 217, as shown generally in FIG. 2-3. Wires 215, 216 are disposed within grooves 219, defined along the non-conductive core 217. FIG. 8-3 shows an exploded isometric view of the compound shaft assembly 307. A wire 216 is attached to the contact ring 207 and extends underneath the contact ring 207, located distally from the contact ring 207. Additionally, a wire 215 is attached to the contact ring 207.

An adaptor 213 is normally snapped, or otherwise attached, at a distal end of the compound shaft assembly 307 to secure wires 215, 216 which are bent, as shown in FIG. 8-3. This reduces flexure of the bent portions 220.

Figures 1A, 9:
FIG. 9-1a shows a side view of a non-conductive core for use with two rings.
Figures 1B, 9:
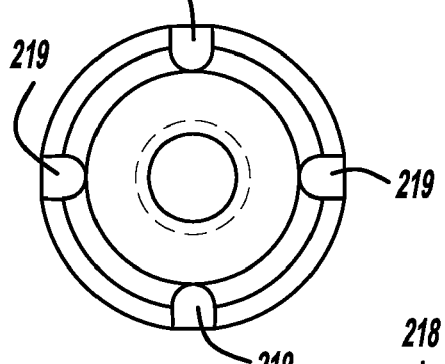
Figures 1C, 9:
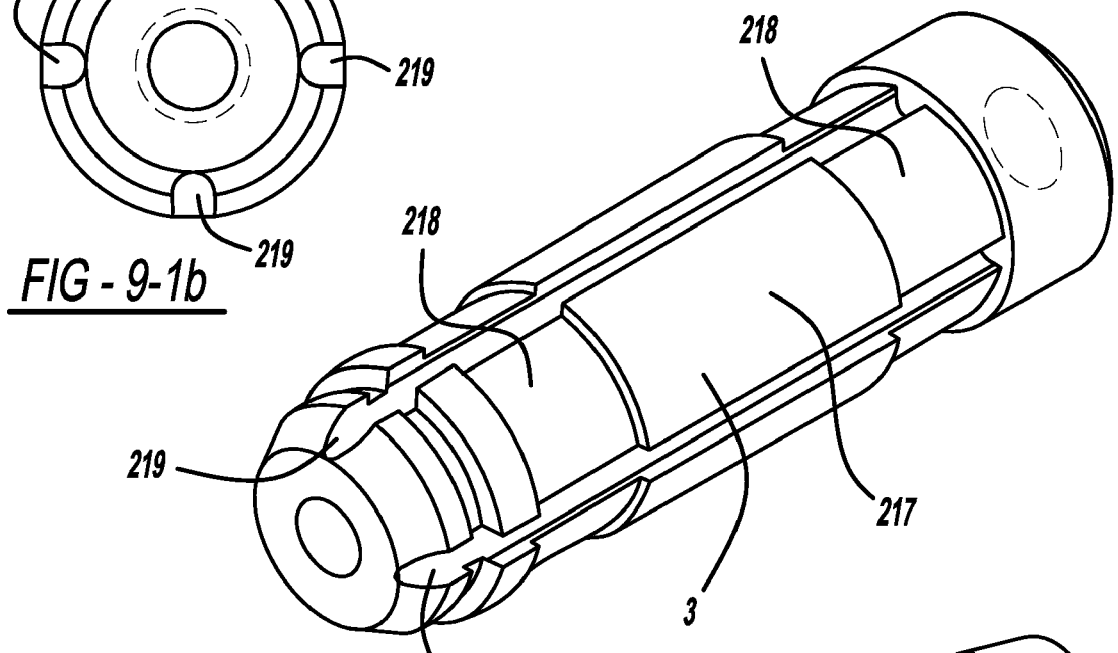
Figures 2, 9:
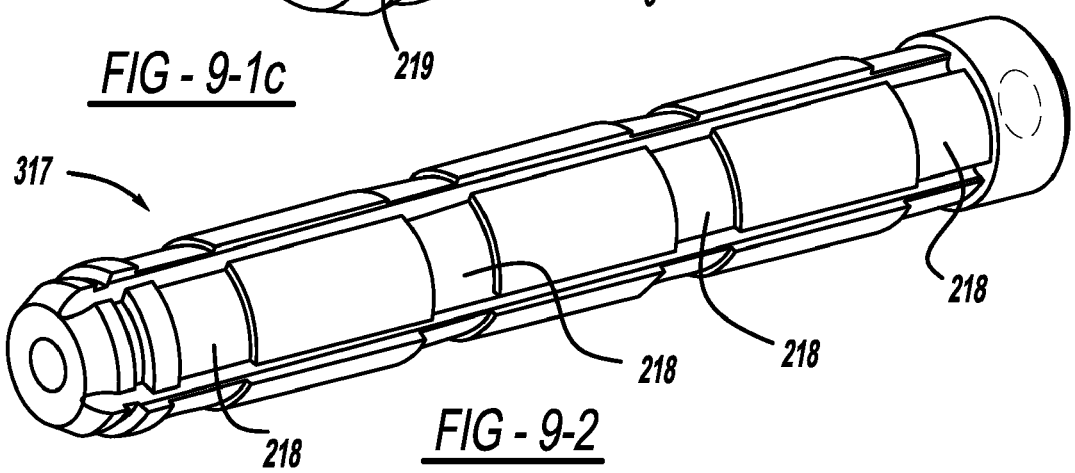

FIGS. 9-1a, 9-1b, and 9-1c show various views of the non-conductive core 217. FIG. 9-2 shows another embodiment of a non-conductive core 217 which defines four recesses 218 and a through-hole. The additional two recesses allow the non-conductive core 217 to be assembled for up to five live wires.

Figures 3A, 9:
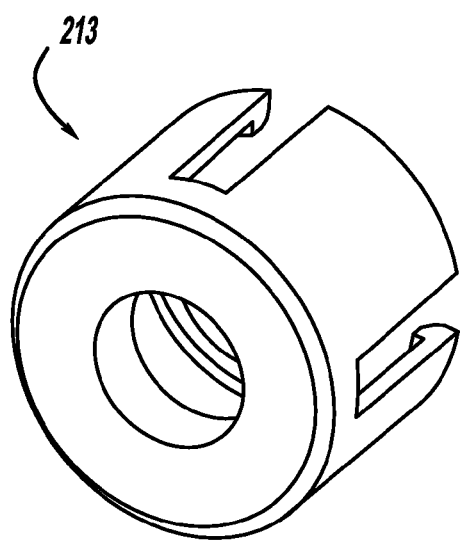
Figures 3B, 9:
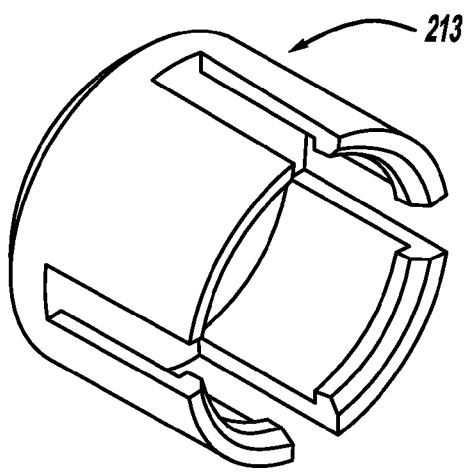
Figures 3C, 9:
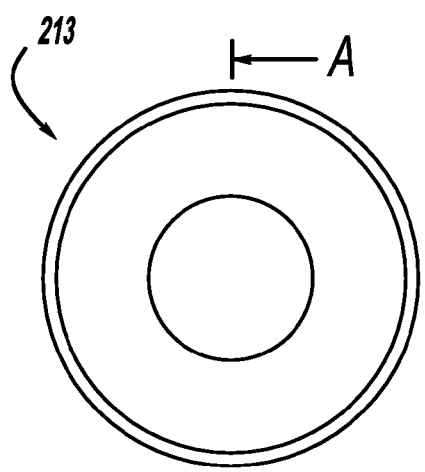
Figures 3D, 9:
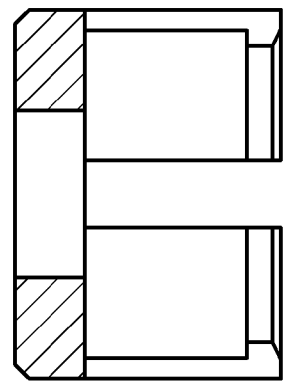
Figures 4, 9:
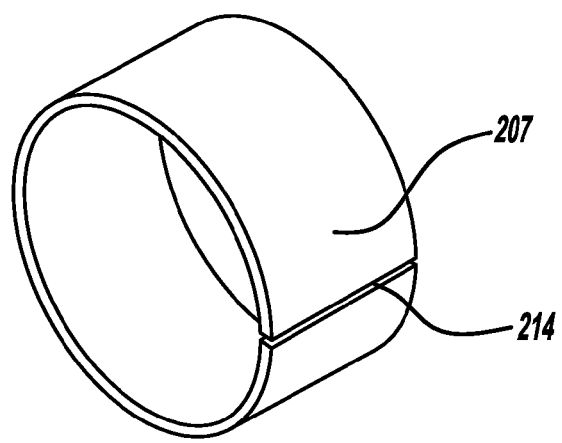

FIGS. 9-3a-d shows views of the adaptor 213, preferably from non-conductive, elastic material. FIG. 9-4 shows a typical contact ring 207 defining a slot 214. The contact ring 207 is preferably formed from elastic, conductive material, which allows it to be resilient such that it expands over the non-conducting core 217 and snaps back to its original size while resting in the recess 218.

While the invention has been described with reference to an exemplary embodiment, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A forceps system connectable to a power source, said system comprising:
    a handle body;
    a surgical device, a portion of the surgical device being removably disposed within the handle body, another portion of the surgical device being operably associated with a pair of jaw members; and
    at least one handle member pivotally attached to the handle body for articulating the jaw members on the surgical device; and wherein
    the surgical device includes
        an adaptor body engagable to the handle body, a portion of the adaptor body including an area defining a hollow passage,
        a compound shaft assembly disposed at least partially within the hollow passage of the adaptor body and operatively connected to the jaw members and the at least one handle member,
        the adaptor body defining a groove thereon and extending therearound and an aperture extending from the groove,
        an adaptor body spring contact disposed within the aperture and thus removable from the handle body as the surgical devices is removed from the handle body and electrically connected to the compound shaft assembly for conducting electrical current from the power source to the compound shaft assembly when disposed within the handle body, and
        a contact ring disposed within the groove and coupled to the adaptor body spring contact for compressing the adaptor body spring contact and conducting electrical current therethrough.

2. The system according to claim 1, wherein the adaptor body is comprised of a non-conductive material selected from the group consisting of polymers, ceramics, and combinations thereof.

3. The system according to claim 1, wherein the surgical device is operable to rotate within the handle body while retaining continuous electrical contact from the power source.

4. The system according to claim 1, wherein the surgical device further comprises at least one wire disposed within the hollow passage for providing an auxiliary function.

5. The system according to claim 1, wherein the surgical device is operated in a monopolar manner.

6. The system according to claim 1, wherein the surgical device is operated in a bipolar manner.

7. The system according to claim 1, wherein the handle body includes a power plug assembly electrically connectable to the power source.

8. The system according to claim 7, wherein the handle body includes a handle body spring contact electrically connected between the power plug assembly and the contact ring of the adaptor body.

9. The system as set forth in claim 1 wherein the adaptor body further defines a second groove extending therearound and a second aperture extending from the second groove, and the adaptor body further comprises a second adaptor body spring contact disposed within the second aperture, and a second contact ring disposed within the second groove and electrically connected to the second adaptor body spring contact for compressing the second adaptor body spring contact and conducting electrical current therethrough.

10. The system as set forth in claim 1 wherein the compound shaft assembly is reciprocally movable within the hollow passage of the adaptor body to affect movement of the jaw members in response to movement of the at least one handle member.

* * * * *